US012507742B2

(12) United States Patent
Mitera et al.

(10) Patent No.: US 12,507,742 B2
(45) Date of Patent: Dec. 30, 2025

(54) BELT AND CLOTHING

(71) Applicants: MITSUFUJI CORPORATION, Kyoto (JP); SUMITOMO BAKELITE CO., LTD., Tokyo (JP)

(72) Inventors: Hideyuki Mitera, Soraku-gun (JP); Jun Okada, Tokyo (JP); Motoki Sato, Tokyo (JP); Yumiko Yamanoi, Tokyo (JP)

(73) Assignees: MITSUFUJI CORPORATION, Kyoto (JP); SUMITOMO BAKELITE CO., LTD., Tokyo (JP)

( * ) Notice: Subject to any disclaimer, the term of this patent is extended or adjusted under 35 U.S.C. 154(b) by 0 days.

(21) Appl. No.: 18/859,730

(22) PCT Filed: Apr. 21, 2023

(86) PCT No.: PCT/JP2023/015974
§ 371 (c)(1),
(2) Date: Oct. 24, 2024

(87) PCT Pub. No.: WO2023/210538
PCT Pub. Date: Nov. 2, 2023

(65) Prior Publication Data

US 2025/0194705 A1 Jun. 19, 2025

(30) Foreign Application Priority Data

Apr. 26, 2022 (JP) ................................ 2022-072497

(51) Int. Cl.
*A41D 1/00* (2018.01)
*A41F 9/00* (2006.01)
*A61B 5/00* (2006.01)

(52) U.S. Cl.
CPC .............. *A41D 1/002* (2013.01); *A41F 9/002* (2013.01); *A61B 5/6805* (2013.01); *A61B 2562/164* (2013.01)

(58) Field of Classification Search
CPC .. A41D 1/002; A61B 5/6805; A61B 2562/164
See application file for complete search history.

(56) References Cited

U.S. PATENT DOCUMENTS 5,906,004 A * 5/1999 Lebby .................. D03D 15/242 2/905
2015/0054941 A1* 2/2015 Ogawa .............. G01N 21/9501 348/87

(Continued)

FOREIGN PATENT DOCUMENTS

JP 2007-527956 A 10/2007
JP 2018-531642 A 11/2018

(Continued)

OTHER PUBLICATIONS

Jun. 13, 2023 International Search Report issued in International Patent Application No. PCT/JP2023/015974.

(Continued)

*Primary Examiner* — Tajash D Patel
(74) *Attorney, Agent, or Firm* — Oliff PLC

(57) ABSTRACT

A belt or clothing using an electrode having higher noise resistance and higher durability than an electrode formed of only a conductive fiber fabric or a conductive elastomer fabric. Clothing includes an electrode and an insulating fiber fabric in a detection region. The electrode is inside the detection region of the clothing so as to make contact with the body of the wearer. The insulating fiber fabric is a clothing material worn by the wearer and is a fabric that constitutes most of the clothing. The electrode includes a conductive fiber fabric layer and a conductive elastomer layer. The conductive fiber fabric layer is a fiber fabric (Continued)

formed by weaving or knitting a yarn including conductive fibers having conductivity. The conductive elastomer layer is formed by applying paste including an elastomer composition and a conductive filler onto an inner surface of the conductive fiber fabric layer and drying the paste.

10 Claims, 12 Drawing Sheets

(56) References Cited

U.S. PATENT DOCUMENTS

| | | | | |
|---|---|---|---|---|
| 2017/0056644 | A1 * | 3/2017 | Chahine | A61N 1/36014 |
| 2017/0143977 | A1 * | 5/2017 | Kaib | A61N 1/3904 |
| 2018/0271441 | A1 * | 9/2018 | Dabby | A61B 5/6804 |
| 2019/0022400 | A1 | 1/2019 | Kumar et al. | |
| 2019/0151648 | A1 | 5/2019 | Hatakeyama et al. | |
| 2022/0133199 | A1 | 5/2022 | Takarada et al. | |
| 2022/0201850 | A1 * | 6/2022 | Abe | A41D 1/002 |
| 2023/0010845 | A1 * | 1/2023 | Wohnsdorf | H05K 1/038 |
| 2025/0082241 | A1 * | 3/2025 | Hergenrother | A61P 43/00 |

FOREIGN PATENT DOCUMENTS

| | | | | | |
|---|---|---|---|---|---|
| JP | 2019-093118 | A | | 6/2019 | |
| TW | M568050 | U | | 10/2018 | |
| TW | 202038855 | A | | 11/2020 | |
| WO | WO-9964657 | A2 | * | 12/1999 | D06M 15/55 |
| WO | 2004/107831 | A2 | | 12/2004 | |
| WO | WO-2012110954 | A1 | * | 8/2012 | A61B 5/6804 |
| WO | 2017/035502 | A1 | | 3/2017 | |
| WO | WO-2019222846 | A1 | * | 11/2019 | A61B 5/4872 |
| WO | WO-2020099906 | A1 | * | 5/2020 | A61B 5/7221 |
| WO | WO-2020179845 | A1 | * | 9/2020 | A61B 5/27 |
| WO | WO-2022080417 | A1 | * | 4/2022 | A41D 13/1281 |
| WO | WO-2022134081 | A1 | * | 6/2022 | A61B 5/252 |

OTHER PUBLICATIONS

Jun. 13, 2023 Written Opinion issued in International Patent Application No. PCT/JP2023/015974.

Oct. 18, 2023 Office Action issued Taiwanese Patent Application No. 112115370.

May 29, 2024 Office Action issued Taiwanese Patent Application No. 112115370.

Aug. 11, 2025 Extended European Search Report issued in European Application No. 23796280.8.

* cited by examiner

BELT AND CLOTHING

TECHNICAL FIELD

The present invention relates to a belt and clothing having an electrode capable of detecting a biological potential.

BACKGROUND ART

A fiber fabric using a conductive fiber has been developed for detecting a biological potential of a wearer. Patent Document 1 discloses a fiber fabric interface formed by separately weaving a conductive fiber, which is selectively exposed, and a non-conductive fiber, which imparts elasticity to a fiber structure, in combination.

CITATION LIST

Patent Document

Patent Document 1: PCT Japanese Translation Patent Publication No. 2007-527956

SUMMARY OF THE INVENTION

Problems to be Solved by the Invention

As described in Patent Document 1, for example, the fiber fabric interface, which is formed by weaving a yarn including fibers having conductivity (conductive fibers) has irregularities specific to the fibers on a surface, and thus has low adhesiveness to a body. Therefore, a conventional electrode such as a fiber fabric interface may pick up noise due to body movement. In addition, a sheet resistance of a conventional electrode is about $10^{-1}\Omega/\square$.

Further, the fiber fabric interface may be used while being knitted into a garment, but when the garment is washed multiple times, a part of the fiber fabric interface is peeled off and falls off, thereby losing its conductivity and not allowing the fiber fabric interface to function. In particular, since a detergent and a linen solution used for washing include various acidic chemicals and alkaline chemicals, the fiber fabric interface may react with the chemicals during washing, thereby losing its conductivity. The noise resistance in the body movement and the durability against washing and the like are not limited to the woven or knitted yarn, and are problems related to the entire fiber fabric interface including, for example, a nonwoven fabric and the like.

Meanwhile, an electrode for measuring a biological potential and the like includes not only the fiber fabric interface but also a conductive elastomer fabric. However, an electrode formed of only the conductive elastomer fabric also has problems of noise resistance and durability as in the fiber fabric interface.

An object of the present invention is to provide a belt or clothing using an electrode having higher noise resistance and higher durability than an electrode formed of only a conductive fiber fabric or a conductive elastomer fabric.

Means for Solving the Problems

Clothing according to a first aspect of the present invention is clothing including: a clothing material worn by a wearer; and an electrode provided at a position of a surface of the clothing material making contact with a body of the wearer upon wearing, in which the electrode includes a conductive fiber fabric layer, which is a fiber fabric having conductivity, the electrode including a conductive fiber fabric layer, which is a fiber fabric having conductivity, and a conductive elastomer layer formed on at least one surface of the conductive fiber fabric layer and including an elastomer composition and a conductive filler.

The clothing according to a second aspect of the present invention is the clothing according to the first aspect, in which the electrode is provided at a position that makes contact with a site of a torso of the wearer at the same height as a xiphoid process.

A belt according to a third aspect of the present invention is a belt including: a belt member having stretchability; and an electrode provided at a position of a surface of the belt member making contact with a body of a wearer when the belt member is wound around the wearer, in which the electrode includes a conductive fiber fabric layer, which is a fiber fabric having conductivity, the electrode includes a conductive fiber fabric layer, which is a fiber fabric having conductivity, and a conductive elastomer layer formed on at least one surface of the conductive fiber fabric layer and including an elastomer composition and a conductive filler.

The belt according to a fourth aspect of the present invention is the belt according to the third aspect, in which the electrode is provided at a position that makes contact with a site of a torso of the wearer at the same height as a xiphoid process.

Advantageous Effect of the Invention

According to the invention of the present application, noise resistance and durability are improved as compared with a belt or clothing formed of only the conductive fiber fabric or the conductive elastomer fabric.

MODE FOR CARRYING OUT THE INVENTION

Embodiment

<Appearance of Clothing>

Figure 1:
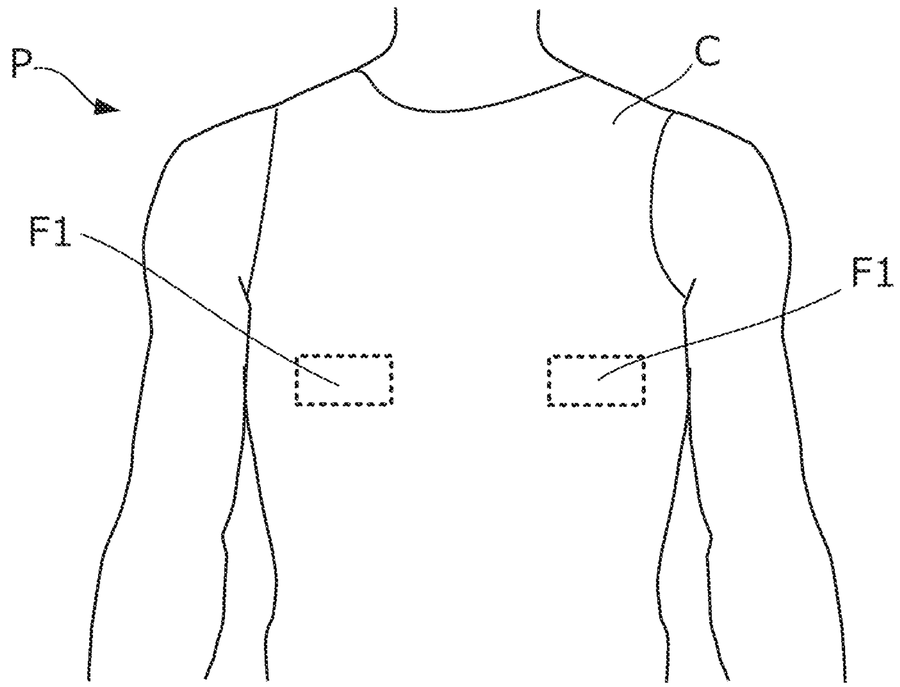
FIG. 1 is a view illustrating an appearance of clothing C according to the present embodiment.

FIG. 1 is a view illustrating an appearance of clothing C according to the present embodiment. The clothing C is worn by a wearer P and comes into contact with a body of the wearer P to detect a biological potential.

Biological information is information obtained from the detected biological potential, and examples thereof include electrocardiogram, heart rate, respiration, pulse wave, body temperature, electromyogram, brain wave, eye potential, blood pressure, sweating amount, blood sugar level, humidity, and the like. The biological information may be any information obtained from the body of the wearer P by making contact with an electrode region. In the following description, the biological information is an electrocardiogram. In addition, in the following description, the "inside" of the clothing C and the like is a side close to the body of the wearer P, and the "outside" is a side farther from the body of the wearer P.

The clothing C illustrated in FIG. 1 is a garment worn on an upper body of the wearer P. A detection region F1 is provided on a front surface of the clothing C between the chest and the abdomen of the wearer P.

<Configuration of Electrode>

Figure 2:
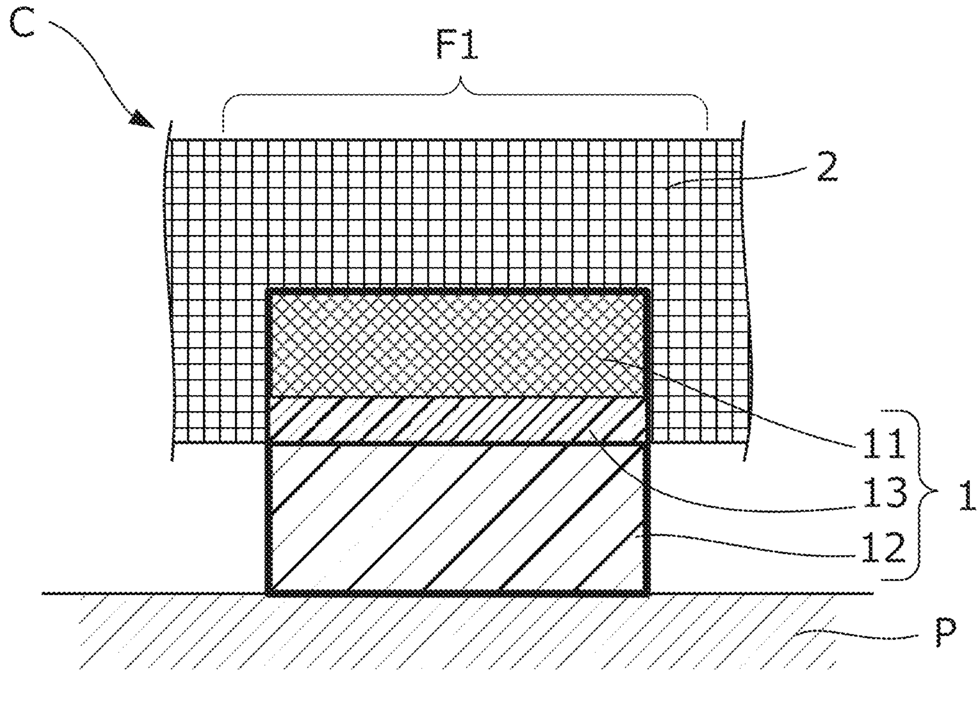
FIG. 2 is a view illustrating an example of a cross-section of a detection region F1 of the clothing C.

FIG. 2 is a view illustrating an example of a cross-section of a detection region F1 of the clothing C. As illustrated in FIG. 2, the clothing C has an electrode 1 and an insulating fiber fabric 2 in the detection region F1. The electrode 1 is provided inside the detection region F1 of the clothing C so as to make contact with the body of the wearer P. Therefore, the clothing C is an example of clothing including a clothing material worn by a wearer and an electrode provided at a position of a surface of the clothing material that makes contact with the body of the wearer.

The clothing C may include a transmitter that transmits a biological signal detected by the electrode 1 to an external device, a wire that communicatively connects the transmitter and the electrode 1 to each other, and an insulating member that protects the wire and the electrode 1 and the like. The insulating member is, for example, a urethane sheet or the like that is adhered to the insulating fiber fabric 2 by heating and pressing.

The insulating fiber fabric 2 is a clothing material worn by the wearer P and is a fabric that constitutes most of the clothing C. The insulating fiber fabric 2 is a fiber fabric formed by weaving or knitting fibers (referred to as insulating fibers) that cannot easily transmit electricity. The insulating fiber fabric 2 is, for example, a knitted fabric, a woven fabric, a nonwoven fabric, or the like.

Figure 3:
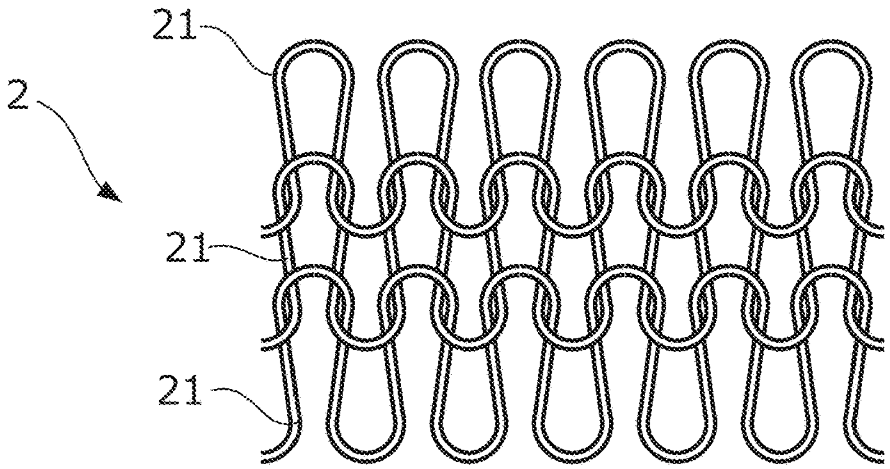
FIG. 3 is a view illustrating an example of a configuration of an insulating fiber fabric 2.

FIG. 3 is a view illustrating an example of a configuration of the insulating fiber fabric 2. The insulating fiber fabric 2 illustrated in FIG. 3 is formed by knitting insulating fibers 21.

It is desirable that the insulating fiber 21 is a fiber having high elasticity (elastic fiber) so as to adhere easily to the body of the wearer P. As the elastic fiber, a fiber having a stretch ratio of at least 50% or more is desirable. The elastic fiber is, for example, polyurethane. In addition, the elastic fiber used for the insulating fiber 21 is not limited to polyurethane, and may be, for example, an elastic polyester, a natural rubber fiber, or a heat-shrinkable nylon, and the like. In addition, the insulating fiber 21 may be a composite yarn formed of a plurality of kinds of insulating fibers.

The electrode 1 illustrated in FIG. 2 includes a conductive fiber fabric layer 11, a conductive elastomer layer 12, and an immersion layer 13. In the electrode 1, the conductive fiber fabric layer 11 is the outermost layer, and the conductive elastomer layer 12 is the innermost layer. The immersion layer 13 is a layer included in the conductive fiber fabric layer 11, and is a layer interposed between the conductive fiber fabric layer 11 and the conductive elastomer layer 12.

The conductive fiber fabric layer 11 is an example of a conductive fiber fabric layer as a fiber fabric having conductivity. In this case, the conductive fiber fabric layer 11 is a fiber fabric formed by weaving or knitting a yarn including fibers having conductivity (referred to as conductive fibers). The conductive fiber fabric layer 11 illustrated in FIG. 2 is formed integrally with the insulating fiber fabric 2. The conductive fiber fabric layer 11 is not limited to being formed integrally with the insulating fiber fabric 2. The conductive fiber fabric layer 11 may be formed, for example, as a knitted fabric, a woven fabric, or the like using a yarn including conductive fibers separately from the insulating fiber fabric 2, and may be sewn to the insulating fiber fabric 2.

Figure 4:
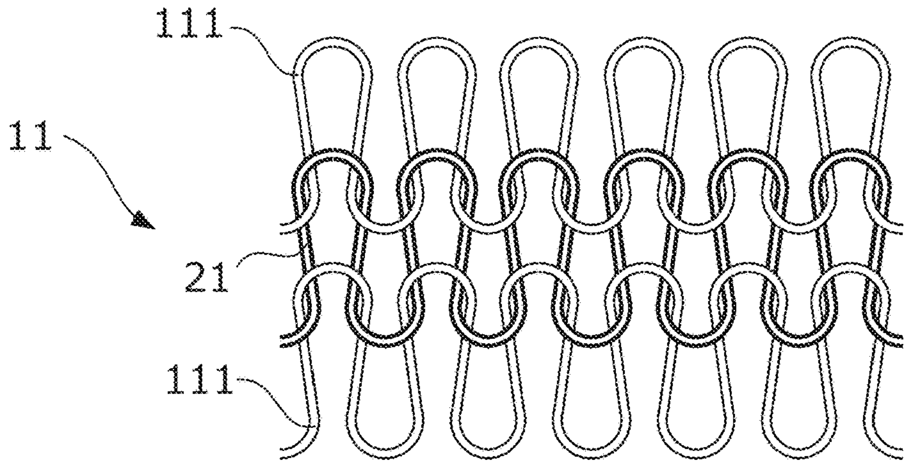
FIG. 4 is a view illustrating an example of a configuration of a conductive fiber fabric layer 11.

FIG. 4 is a view illustrating an example of a configuration of the conductive fiber fabric layer 11. For example, as illustrated in FIG. 4, the conductive fiber fabric layer 11 is formed by knitting a conductive composite yarn 111 into the above-described insulating fiber 21. The conductive fiber fabric layer 11 may be integrally formed with the insulating fiber fabric 2 such that there is no step therebetween by knitting the common insulating fibers 21.

Figure 5:
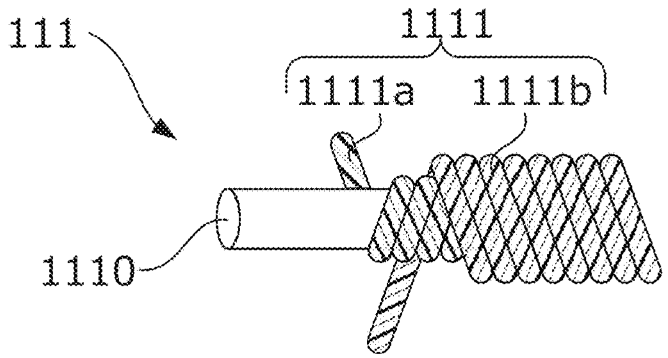
FIG. 5 is a view illustrating an example of a conductive composite yarn 111.

FIG. 5 is a view illustrating an example of the conductive composite yarn 111. The conductive composite yarn 111 is a composite yarn formed by winding the conductive fiber 1111 around an elastic fiber 1110.

The elastic fiber 1110 is a fiber having relatively high elasticity. As the elastic fiber 1110, a fiber having a stretch ratio of at least 50% or more is desirable. The elastic fiber is 1110, for example, polyurethane. The elastic fiber 1110 may be, for example, an elastic polyester, a natural rubber fiber, a heat-shrinkable nylon, or the like. In addition, the elastic fiber 1110 may be commonly used for the insulating fiber 21.

The conductive fiber 1111 is a fiber having conductivity, and is obtained by adding a conductive material to a fiber having non-conductivity (referred to as a non-conductive fiber). The conductive material is, for example, a metal such as silver, copper, stainless steel, nickel, or aluminum. In addition, the conductive material may be a non-metal such as carbon or a conductive polymer.

That is, the conductive composite yarn 111 illustrated in FIG. 5 is an example of a yarn including a conductive fiber, and is an example of a conductive composite yarn obtained by winding the conductive fiber around the elastic fiber. The conductive fiber fabric layer 11 formed by knitting the conductive composite yarn 111 into the insulating fiber 21 is an example of a conductive fiber fabric layer formed by knitting a yarn including conductive fibers into an insulating fiber that insulates electricity.

The conductive material is added to the non-conductive fiber by, for example, a wet film treatment such as a non-electrolytic metal plating treatment. The conductive fiber 1111 illustrated in FIG. 5 is, for example, a yarn obtained by performing silver plating on nylon. In order to stably detect the biological potential, a ratio of silver to nylon in the conductive fiber 1111 may be 10% by mass or more, desirably 20% by mass or more, and more desirably 30% by mass or more.

The method for adding the conductive material to the non-conductive fiber is not limited to the wet film treatment, and may be, for example, vapor deposition, sputtering, adhesion of metal foil, impregnation, or the like. The conductive fiber 1111 may be formed by, for example, impregnating an acrylic fiber with copper sulfide.

The non-conductive fiber used for the conductive fiber 1111 is, for example, nylon. The non-conductive fiber may be a fiber having a conductivity below a determined threshold. Therefore, the non-conductive fiber may be, for example, a natural fiber such as cellulose or raw silk, or another synthetic fiber. By using the natural fiber in the non-conductive fiber, the clothing C can be worn by the wearer P even in a case where the wearer P has an allergy to the synthetic fiber.

The conductive fiber 1111 may not include the non-conductive fiber as long as the conductive fiber 1111 has conductivity. In addition, the conductive fiber fabric layer 11 may not be knitted into the insulating fiber 21 as long as the conductive fiber 1111 has conductivity as a whole. For example, the conductive fiber fabric layer 11 may be formed by knitting only the conductive composite yarn 111.

The conductive composite yarn 111 illustrated in FIG. 5 is formed by doubly winding the conductive fiber 1111 around the elastic fiber 1110 serving as a core yarn. That is, the conductive composite yarn 111 is formed of a double-covered yarn.

As illustrated in FIG. 5, the conductive composite yarn 111 is formed by first winding a lower winding yarn 1111*a*, which is the conductive fiber 1111, around the elastic fiber 1110, and then winding an upper winding yarn 1111*b*, which is the conductive fiber 1111, on the lower winding yarn 1111*a* in the opposite direction.

The conductive elastomer layer 12 is formed by applying a paste onto an inner surface of the conductive fiber fabric layer 11 and drying the paste.

Figure 6:
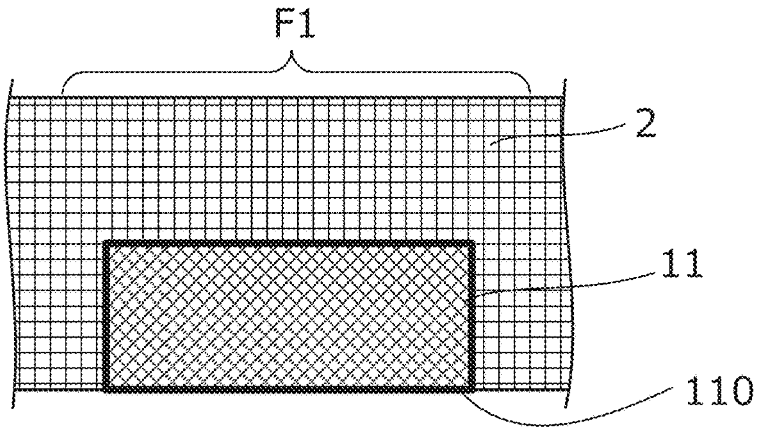
FIG. 6 is a view illustrating a state of the conductive fiber fabric layer 11 before a paste is applied.

FIG. 6 is a view illustrating a state of the conductive fiber fabric layer 11 before the paste is applied. As described above, the conductive fiber fabric layer 11 is formed on at least one surface of the insulating fiber fabric 2 such that no step is formed, for example. The surface 110 is a surface on a side close to the wearer P (not illustrated in FIG. 6), that is, an inner surface of the conductive fiber fabric layer 11.

Figure 7:
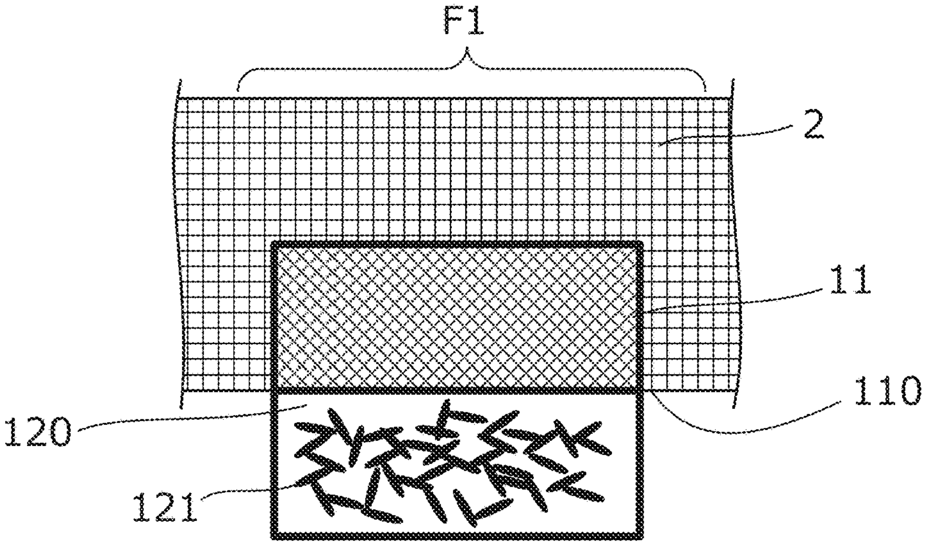
FIG. 7 is a view illustrating a state of the conductive fiber fabric layer 11 when the paste is applied.

FIG. 7 is a view illustrating a state of the conductive fiber fabric layer 11 when the paste is applied. As illustrated in FIG. 7, a paste including an elastomer composition 120 and a conductive filler 121 is applied to the inner surface 110 of the conductive fiber fabric layer 11.

The elastomer composition 120 illustrated in FIG. 7 is obtained by dissolving an elastomer in a solvent. Examples of the elastomer include a silicone rubber, a fluororubber, a nitrile rubber, an acrylic rubber, a styrene rubber, a chloroprene rubber, an ethylene propylene rubber, a urethane rubber, and the like.

Examples of the solvent for dissolving the above-described elastomer include aliphatic hydrocarbons, aromatic hydrocarbons, ethers, haloalkanes, carboxylic acid amides, sulfoxides, and the like.

Examples of the aliphatic hydrocarbons include pentane, hexane, cyclohexane, heptane, methylcyclohexane, ethylcyclohexane, octane, decane, tetradecane, and the like. Examples of the aromatic hydrocarbons include benzene, toluene, ethylbenzene, xylene, trifluoromethylbenzene, benzotrifluoride, and the like. Examples of the ethers include diethyl ether, diisopropyl ether, dibutyl ether, cyclopentylmethyl ether, cyclopentylethyl ether, ethylene glycol dimethyl ether, ethylene glycol diethyl ether, diethylene glycol dimethyl ether, 1,4-dioxane, 1,3-dioxane, tetrahydrofuran, and the like. Examples of the haloalkanes include dichloromethane, chloroform, 1,1-dichloroethane, 1,2-dichloroethane, 1,1,1-trichloroethane, 1,1,2-trichloroethane, and the like. Examples of the carboxylic acid amides include N,N-dimethylformamide, N,N-dimethylacetamide, and the like. Examples of the sulfoxides include dimethyl sulfoxide, diethyl sulfoxide, and the like. The solvent may be one of these solvents, or may be a solvent obtained by mixing two or more of these solvents at an arbitrary ratio.

A content of the elastomer in the paste is preferably 3% by mass or more, more preferably 5% by mass or more, and still more preferably 7% by mass or more with respect to the total solid content of the paste. The content of the elastomer in the paste is preferably 30% by mass or less, more preferably 25% by mass or less, and still more preferably 20% by mass or less with respect to the total solid content of the paste.

The conductive filler 121 illustrated in FIG. 7 is a fine solid having conductivity. The conductive filler 121 is not particularly limited, and includes, for example, at least one type of copper, silver, gold, nickel, tin, lead, zinc, bismuth, antimony, or metal powder obtained by alloying thereof, a conductive organic compound, and a conductive carbon material, or two or more types thereof.

From the viewpoint of high conductivity or high availability, the conductive filler preferably includes silver or copper. That is, the conductive filler preferably includes silver powder or copper powder. The conductive filler may be coated with another metal.

The shape of the conductive filler is not limited, and the shape of a conductive filler that has been conventionally used, such as a dendritic shape, a spherical shape, and a scale shape, can be used.

The above-described paste is produced by adding the conductive filler 121 to the elastomer composition 120. Particles of the added conductive filler 121 makes contact with each other in the elastomer composition 120 to impart conductivity to the entire paste.

A content of the conductive filler in the paste is preferably 60% by mass or more, more preferably 65% by mass or more, and still more preferably 70% by mass or more with respect to the total solid content of the paste. In addition, the content of the conductive filler in the paste is preferably 90% by mass or less, more preferably 88% by mass or less, and still more preferably 85% by mass or less with respect to the total solid content of the paste.

The above-described paste may include silica particles as necessary. By including the silica particles, it is possible to improve hardness and mechanical strength of a cured product formed of the paste.

A specific surface area of the silica particles is preferably 10 to 400 m2/g, and more preferably 20 to 400 m2/g. In addition, a median diameter D50 thereof is preferably 1 to 100 nm and more preferably 5 to 20 nm. By using silica particles having such a specific surface area and a median diameter, the function of the silica particles described above can be significantly exhibited.

A particle diameter of the silica particles can be defined, for example, as an average value of 200 silica particles, which is optionally selected, by performing image analysis after observing the paste or the cured product with a transmission electron microscope or the like.

The silica particles are not particularly limited, and for example, fumed silica, baked silica, sedimentary silica, or the like can be used.

The silica particles may be used alone or in combination of two or more kinds thereof.

A content of the silica particles in the paste as described above is preferably 1% by mass or more, more preferably 2% by mass or more, and still more preferably 3% by mass or more with respect to the total solid content of the paste. In addition, the content of the silica particles in the paste is preferably 15% by mass or less, more preferably 12% by mass or less, and still more preferably 10% by mass or less with respect to the total solid content of the paste.

By setting the content of the silica particles to the above-described lower limit value or more and the upper limit value or less, the cured product of the paste can have an appropriate mechanical strength. In addition, by setting the content of the silica particles to the above-described upper limit value or less, the cured product can have appropriate conductive properties.

Figure 8:
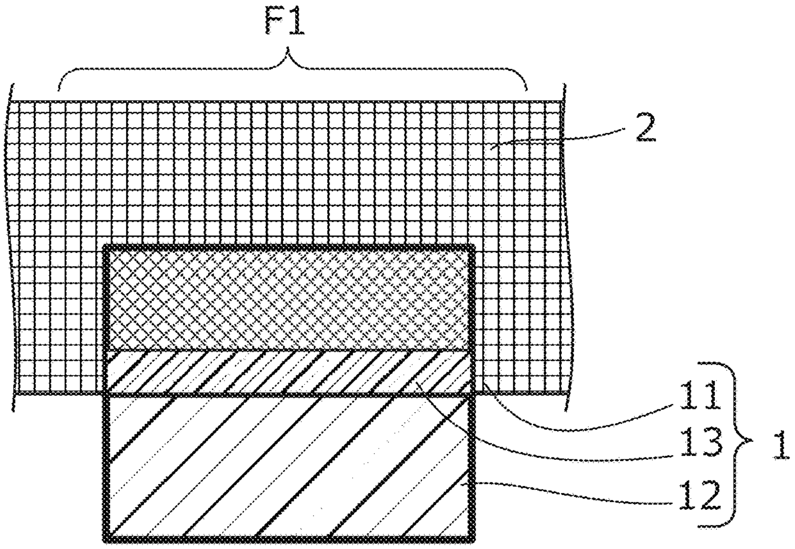
FIG. 8 is a view illustrating a state of an electrode 1 after the paste is dried.

FIG. 8 is a view illustrating a state of an electrode 1 after the paste is dried. For example, when the paste is dried, a certain amount of the solvent volatilizes so that the paste becomes the conductive elastomer layer 12 illustrated in FIG. 8. As a result, the conductive elastomer layer 12 is formed inside the surface 110 of the conductive fiber fabric layer 11. That is, the conductive elastomer layer 12 is an example of a conductive elastomer layer formed on at least one surface of the conductive fiber fabric layer and including an elastomer composition and a conductive filler.

In addition, the surface 110 of the conductive fiber fabric layer 11 is immersed in the applied paste. The immersed paste is dried so that the conductive fiber fabric layer 11 is formed with an immersion layer 13 on a side of the surface 110. The immersion layer 13 contains the elastomer composition 120 and the conductive filler 121 in gaps between fibers of the conductive fiber fabric layer 11. Therefore, the conductive fiber fabric layer 11, which includes the immersion layer 13 on the side of the surface 110, is an example of a conductive fiber fabric layer including an immersion layer in which the elastomer composition and the conductive filler are immersed in at least one surface thereof.

The electrode 1 has the conductive elastomer layer 12 on the innermost side thereof. Since the conductive elastomer layer 12 is formed with the elastomer composition 120, a surface of the conductive elastomer layer 12 is smooth as compared with, for example, the conductive fiber. Therefore, the electrode 1 is more likely to adhere closely to the body of the wearer P without a gap, and is less likely to be affected by noise, as compared with other electrodes that do not include the conductive elastomer layer 12.

In addition, the immersion layer 13 has a configuration in which the conductive filler 121 is electrified with the conductive elastomer layer 12 being intricately incorporated into gaps of the conductive composite yarn 111 forming the conductive fiber fabric layer 11. Therefore, the immersion layer 13 enhances electrification between the conductive fiber fabric layer 11 and the conductive elastomer layer 12.

The electrode 1 was produced in the order of: (1) forming the conductive fiber fabric layer 11 on at least one surface of the insulating fiber fabric 2; (2) applying the paste to the inner surface 110 of the conductive fiber fabric layer 11; and (3) drying the paste to form the conductive elastomer layer 12 (and the immersion layer 13), but the production step of the electrode 1 is not limited thereto. The electrode 1 may be produced, for example, in the order of (2)→(1)→(3) or in the order of (2)→(3)→(1).

In addition, the step (1) is not limited to integrally forming the conductive fiber fabric layer 11 with the insulating fiber fabric 2, as described above. Therefore, for example, the electrode 1 may be produced by the step of: (2) applying the paste to the inner surface 110 of the conductive fiber fabric layer 11, (1) sewing the conductive fiber fabric layer 11 onto at least one surface of the insulating fiber fabric 2, and (3) drying the paste to form the conductive elastomer layer 12.

<Position of Detection Region>

In the present embodiment, since biological information to be detected is the electrocardiogram, the myoelectric potential becomes noise. For example, when the conductive fiber fabric layer 11 is provided in a site close to the pectoralis major muscle, the rectus abdominis muscle, or the like, it is difficult to measure the electrocardiogram because the myoelectric potential affects the electrocardiogram. Therefore, the electrode 1 is provided in a detection region F1 making contact with a site, which is disposed between the chest and the abdomen of the wearer P in the clothing C and is less likely to be affected by the myoelectric potential such as pectoralis major muscle or the rectus abdominis muscle.

Figure 9:
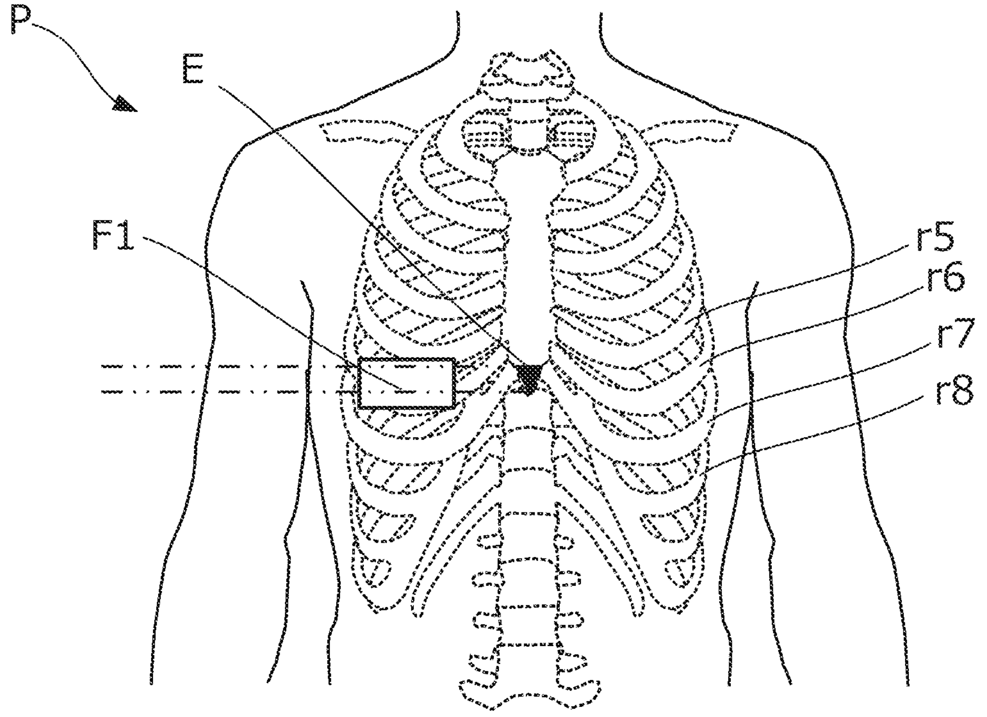
FIG. 9 is a view illustrating an example of a position of the detection region F1.

FIG. 9 is a view illustrating an example of a position of the detection region F1. When the biological information is the electrocardiogram, it is desirable that the detection region F1 is a site that is less likely to be affected by the myoelectric potential such as pectoralis major muscle and the rectus abdominis muscle, as described above. The detection region F1 illustrated in FIG. 9 is a region that makes contact with a skin of a front surface of the torso of the wearer P, which covers a fifth rib r5 to a sixth rib r6.

In addition, the detection region F1 may be a region that makes contact with the skin of the torso of the wearer P at the same height as a xiphoid process E. That is, the electrode 1 provided in the detection region F1 is an example of an electrode that makes contact with a site of the torso of the wearer at the same height as the xiphoid process.

Figure 10:
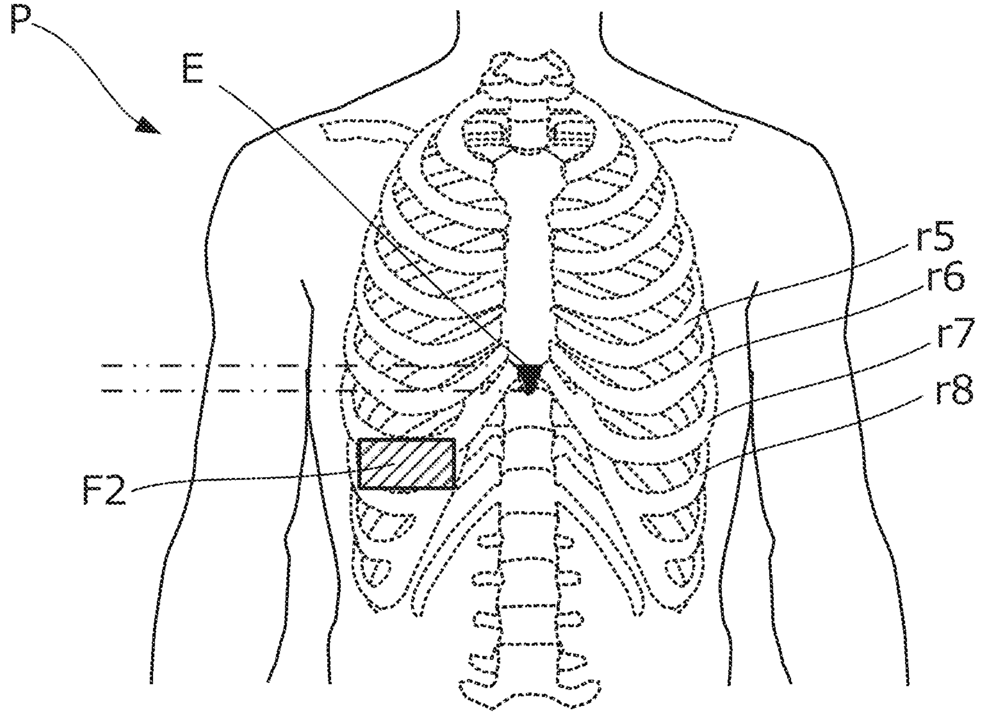
FIG. 10 is a view illustrating an example of a position of a detection region F2.

FIG. 10 is a view illustrating an example of a position of the detection region F2. The detection region F2 is a region where the electrode is provided in the related art. The detection region F2 illustrated in FIG. 10 is provided at a position of the torso of the wearer P which is lower than the xiphoid process E. In addition, the detection region F2 illustrated in FIG. 10 is a region that makes contact with a skin covering a seventh rib r7 to an eighth rib r8.

It has been shown by experiment that noise is reduced in the clothing C in which the electrode 1 is provided in the detection region F1, as compared with the other clothing in which the electrode is provided in the detection region F2.

Modification Example

Although the embodiment has been described above, the contents of the embodiment can be modified as follows. In addition, the following modification examples may be combined.

<1>

In the above-described embodiment, the conductive fiber fabric layer 11 of the electrode 1 uses the conductive composite yarn 111 as a yarn including the conductive fiber, but the yarn is not limited to the composite yarn. For example, the conductive fiber 1111 may be used as it is in the conductive fiber fabric layer 11. The conductive fiber fabric layer 11 may be, for example, a fiber fabric formed by knitting the conductive fiber, which is a yarn obtained by performing silver plating on nylon, into a polyurethane elastic fiber.

<2>

In the above-described embodiment and modification example, the conductive fiber fabric layer 11 is formed by knitting the yarn including conductive fibers, but the conductive fiber fabric layer 11 may be a fiber fabric having conductivity. The conductive fiber fabric layer 11 may be a fiber fabric in which a conductive material is formed on a surface of an insulating fiber fabric having no conductivity or a surface of a non-conductive fiber fabric having a conductivity level that does not reach a certain level. The conductive material is formed, for example, by film deposition by plating.

For example, the conductive fiber fabric layer 11 may be a fiber fabric obtained by performing silver plating on an insulating fabric obtained by knitting nylon and polyurethane. The conductive fiber fabric layer 11 according to the modification example is an example of a conductive fiber fabric layer having a conductive coating layer, in which a conductive coating film is deposited on an insulating fiber fabric formed of insulating fibers that insulate electricity, on at least one surface thereof.

<3>

In the above-described embodiment, the conductive elastomer layer 12 is formed by applying and drying one kind of paste, but the conductive elastomer layer 12 may be formed by sequentially applying two or more kinds of pastes.

Figure 11:
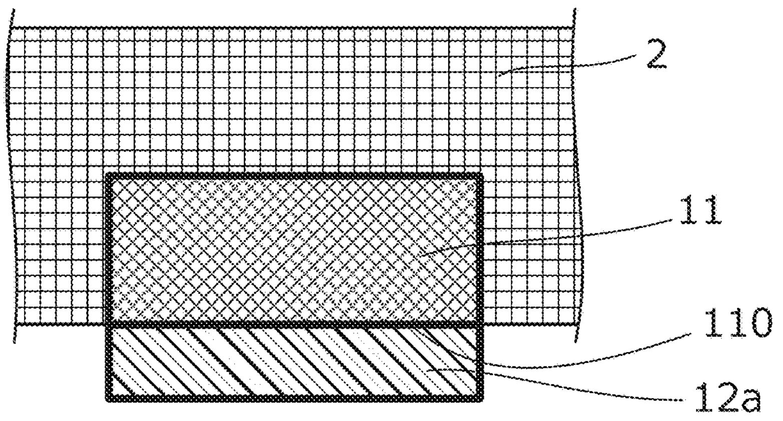
FIG. 11 is a view illustrating an example of an initial stage of formation of a conductive elastomer layer 12 according to a modification example.

FIG. 11 is a view illustrating an example of an initial stage of formation of a conductive elastomer layer 12 according to the modification example. As illustrated in FIG. 11, a first paste is applied onto the surface 110 of the conductive fiber fabric layer 11. The first paste is dried to form a first conductive elastomer layer 12*a*.

Figure 12:
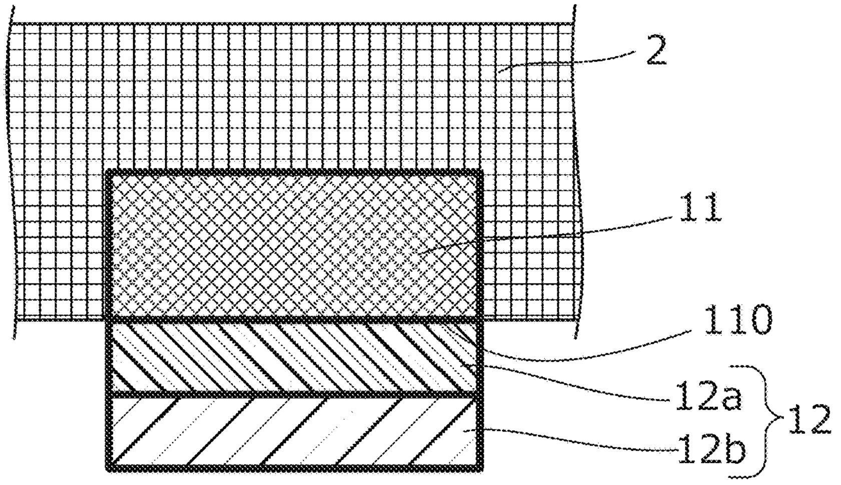
FIG. 12 is a view illustrating an example of a process in which a conductive elastomer layer 12 is being formed according to the modification example.

FIG. 12 is a view illustrating an example of a process in which the conductive elastomer layer 12 is being formed according to the modification example. As illustrated in FIG. 12, a second paste is applied onto a surface of the first conductive elastomer layer 12*a*. The second paste is dried to form a second conductive elastomer layer 12*b*.

Figure 13:
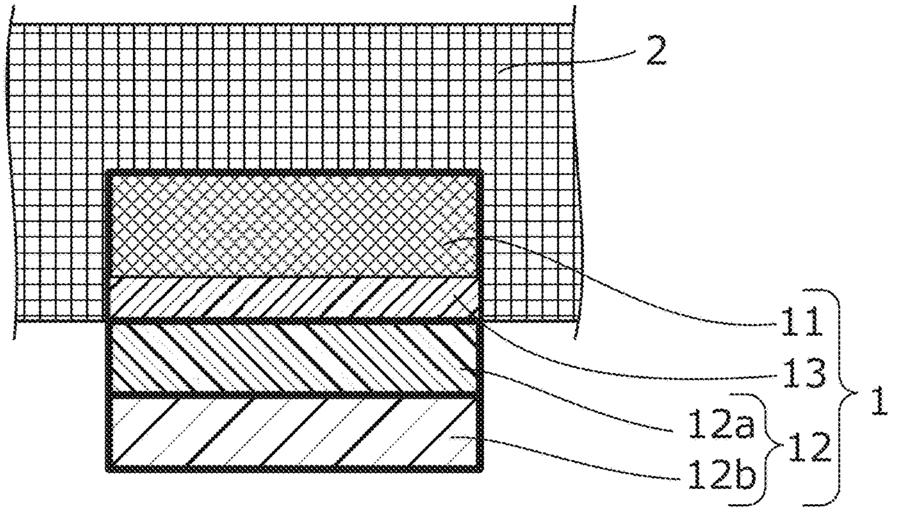
FIG. 13 is a view illustrating an example of a final stage of the conductive elastomer layer 12 according to the modification example.

In addition, the first conductive elastomer layer 12*a* is immersed in the conductive fiber fabric layer 11 during drying to form the immersion layer 13 inside the first conductive elastomer layer 12*a*. FIG. 13 is a view illustrating an example of a final stage of the conductive elastomer layer 12 according to the modification example. The electrode 1 illustrated in FIG. 13 includes the conductive fiber fabric layer 11 having the immersion layer 13 formed on an inside thereof, the first conductive elastomer layer 12*a*, and the second conductive elastomer layer 12*b*. The first conductive elastomer layer 12*a* is formed inside the immersion layer 13. The second conductive elastomer layer 12*b* is formed inside the first conductive elastomer layer 12*a*.

In this case, the first paste and the second paste may have a difference in concentration of the conductive filler 121 (see FIG. 7). For example, the second paste according to the modification example has a higher concentration of the conductive filler 121 as compared with the first paste. That is, the first paste according to the modification example has a lower concentration of the conductive filler as compared with the second paste.

As a result, the first conductive elastomer layer 12*a* is a layer that is closer to the conductive fiber fabric layer 11 than the second conductive elastomer layer 12*b* and has a lower concentration of the conductive filler 121.

That is, the conductive elastomer layer 12 according to the modification example is an example of a conductive elastomer layer having a region in which the concentration of the conductive filler is low as the conductive elastomer layer 12 approaches the conductive fiber fabric layer.

The conductive elastomer layer 12 has a higher concentration of the conductive filler 121 on the side farther from the conductive fiber fabric layer 11 and closer to the body of the wearer P. Therefore, the conductive elastomer layer 12 includes a large amount of the conductive filler 121 and the portion that is easily exposed to impact, friction, and the like is more easily peeled off, whereby it is expected that durability against impact, friction, and the like is shown as compared with the conductive filler 121 having a uniform concentration.

<4>

In the above-described embodiment, the electrode 1 is provided on the clothing C, and may be provided on a belt.

Figure 14:
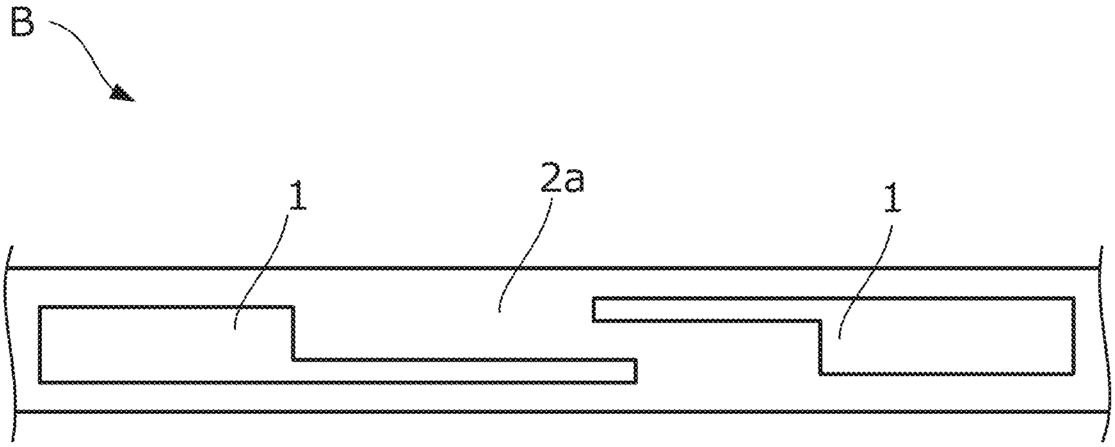
FIG. 14 is a view illustrating an example of a belt B according to the modification example.

FIG. 14 is a view illustrating an example of a belt B according to the modification example. The belt B includes a belt member 2*a* having stretchability and an electrode 1 provided on a surface of the belt member 2*a*.

The electrode 1 is provided at a position making contact with the body of the wearer P when the belt B is wound around the wearer P.

That is, the belt B is an example of a belt including a belt member having stretchability and an electrode provided at a position of a surface of the belt member making contact with the body of the wearer when the belt member is wound around the wearer.

Figure 15:
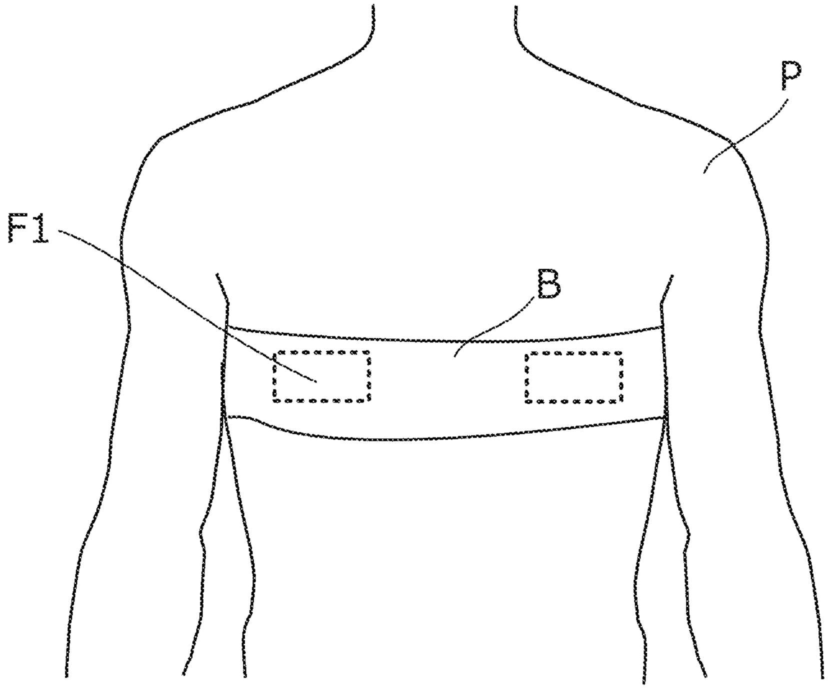
FIG. 15 is a view illustrating an example of a wearing state of the belt B according to the modification example.

FIG. 15 is a view illustrating an example of a wearing state of the belt B according to the modification example. The belt B is wound around between the chest and the abdomen of the wearer P such that the electrode 1 is disposed in the detection region F1. The detection region F1 illustrated in FIG. 15 is disposed at the common position as the detection region F1 illustrated in FIG. 9. That is, the electrode 1 provided on the belt B is an example of an electrode that makes contact with a site of the torso of the wearer at the same height as xiphoid process.

Even when the belt B does not cover the torso of the wearer P like the clothing C, the electrode 1 can make contact with the body of the wearer P in the detection region F1 to detect a biological signal. Even in this case, since the electrode 1 includes the conductive fiber fabric layer 11 and the conductive elastomer layer 12, the electrode 1 is likely to adhere closely to the body of the wearer P and is less likely to be affected by noise.

Experimental Example

<Experiment A (Simulated Washing Experiment)>

<Sample>

The present inventors have carried out an experiment (hereinafter, referred to as Experiment A) in which a sample is subjected to a treatment simulating washing, and an appearance of the sample before and after the treatment is imaged and evaluated. As samples provided for Experiment A, a sample including only AGPoss (registered trademark, the same applies hereinafter) manufactured by Mitsufuji Corporation (hereinafter, referred to as a sample A1) and a sample obtained by printing (coating and drying) DuraQ (registered trademark, the same applies hereinafter) manufactured by Sumitomo Bakelite Co., Ltd. on a surface of AGPoss (hereinafter, referred to as a sample A2) were used. In this case, AGPoss is an example of the conductive fiber fabric layer 11. In addition, DuraQ is an example of the conductive elastomer layer 12. In Experiment A, as AGPoss, a sample obtained by adding 10% by mass or more of silver to a nylon/polyurethane elastic fiber through a plating treatment was used. In addition, in Experiment A, as DuraQ, a paste-like sample, which is obtained by dissolving silicone rubber in a hydrocarbon solvent such as decane or tetradecane, and adding silver powder to the mixture and mixing the same to obtain a solid concentration of about 70% by mass, was used.

The sample A2 was formed by applying a conductive paste in a direction approximately perpendicular to grains of the AGPoss fibers and drying the same. The sample A2 was obtained by forming the DuraQ on a 1.3 cm square area of a surface of the AGPoss. A concentration of the conductive filler in the conductive paste was 86% by mass, and an adhesion amount of the paste was 39.5 mg/cm$^2$ (milligram per square centimeter).

<Flow of Experiment>

Figure 16:
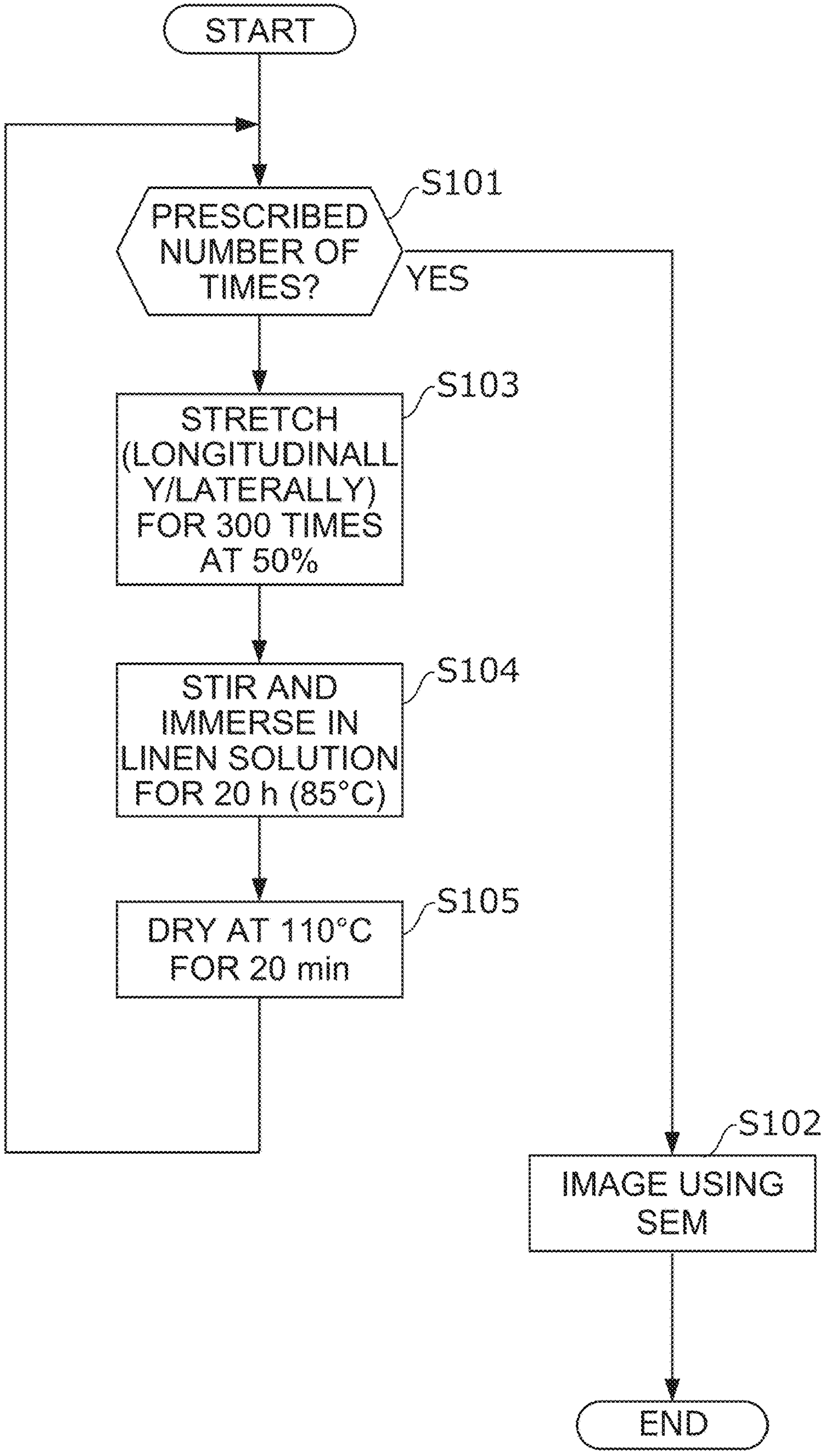
FIG. 16 is a flowchart illustrating a flow of an experiment on an effect of an electrode by a load for simulating washing.

FIG. 16 is a flowchart illustrating a flow of the experiment on an effect of the electrode by a load for simulating washing. The experimenter performed the following steps S101 to S105 to apply a load for simulating washing to the samples.

First, the experimenter determined whether or not the subject had performed a prescribed number of determined treatments (step S101), and when it was determined that the prescribed number of treatments has been performed (step S101; YES), the experimenter imaged the samples using the scanning electron microscope (SEM), and evaluated the samples (step S102).

On the other hand, the experimenter repeated the treatment from step S103 to step S105 while it was determined that the prescribed number of treatments has not been performed (step S101; NO).

First, the experimenter performed expansion and contraction of the samples in a longitudinal direction and a lateral direction 300 times at a stretch ratio of 50% (step S103). In this case, the stretch ratio refers to a percentage of an increased length with respect to a length of the samples under no load. That is, in the stretching experiment, the samples are stretched to a maximum length of 1.5 times.

Next, the experimenter immersed the samples in a linen solution and stirred the samples for 20 hours (step S104). In the linen solution, 1.5 milliliters of hydrogen peroxide and 1.5 milliliters of a 30 w/v % sodium hydroxide aqueous solution were added to 1 liter of water. A temperature of the linen solution was kept at 85° C. According to the present invention, w/v % indicates a proportion of mass (gram) to 100 milliliters of the total volume.

Next, the experimenter dried the samples at 110° C. for 20 minutes (step S105).

Experimental Results

Figure 17:
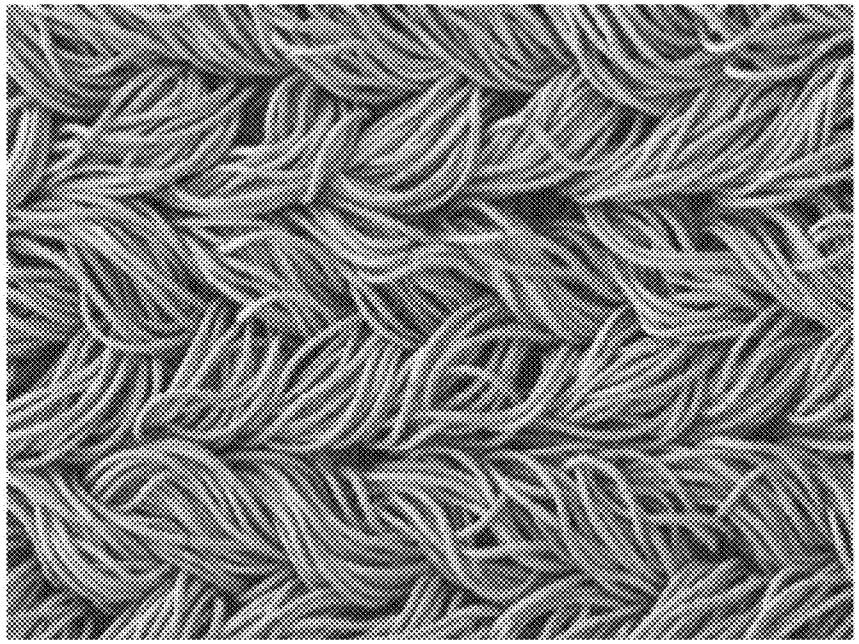
FIG. 17 is an image of a surface of an untreated sample A1.
Figure 18:
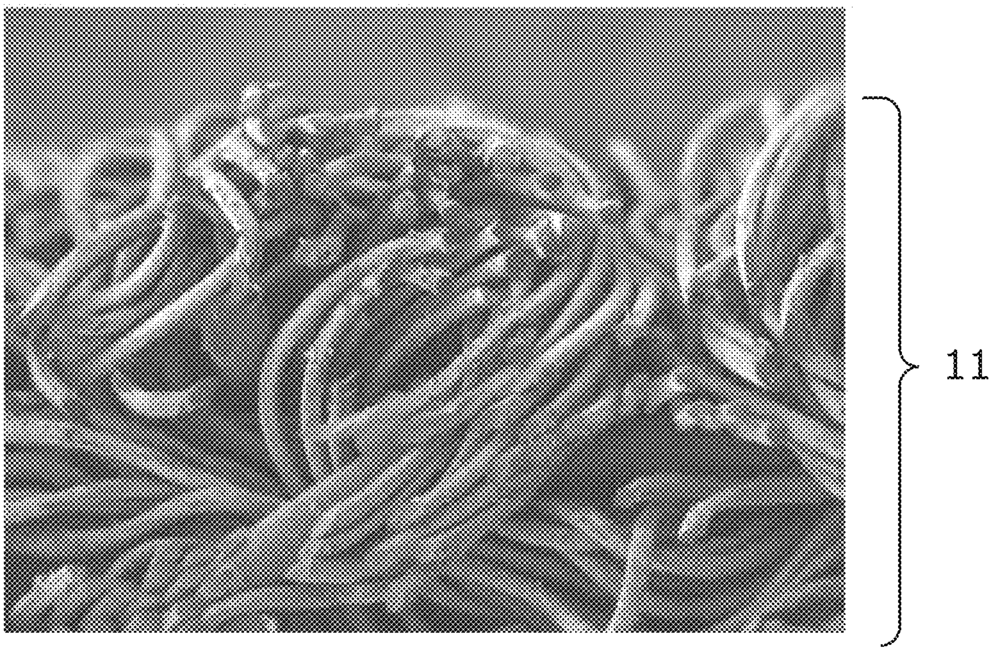
FIG. 18 is an image of a cross-section of the untreated sample A1.

FIG. 17 is an image of a surface of an untreated sample A1. FIG. 18 is an image of a cross-section of the untreated sample A1. Since the samples are untreated, the above-described prescribed number of times is 0. As illustrated in FIGS. 17 and 18, in the untreated state, no damage or the like to the silver plating formed on a surface of the fiber was observed in the sample A1.

Figure 19:
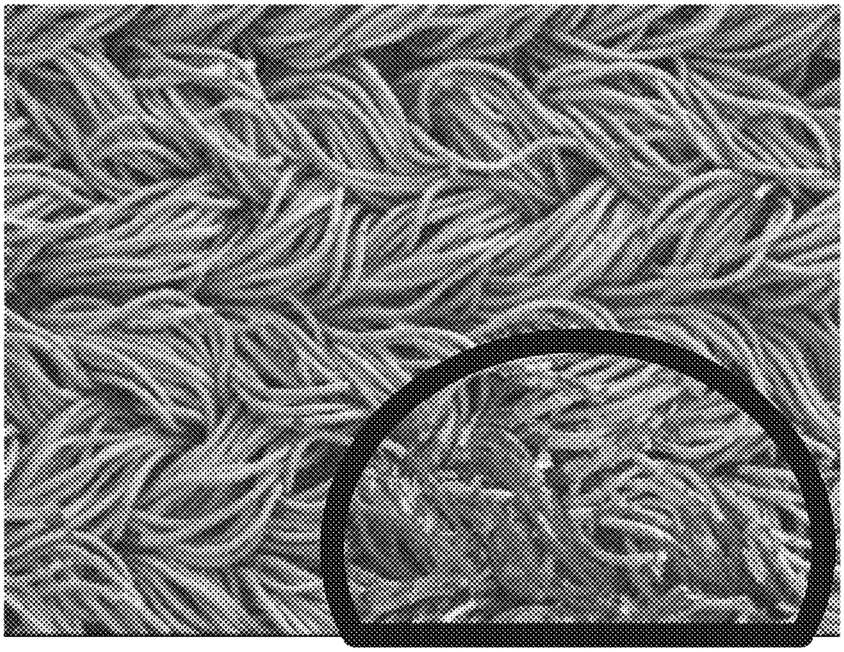
FIG. 19 is an image of a surface of a sample A1 that has been treated five times.
Figure 20:
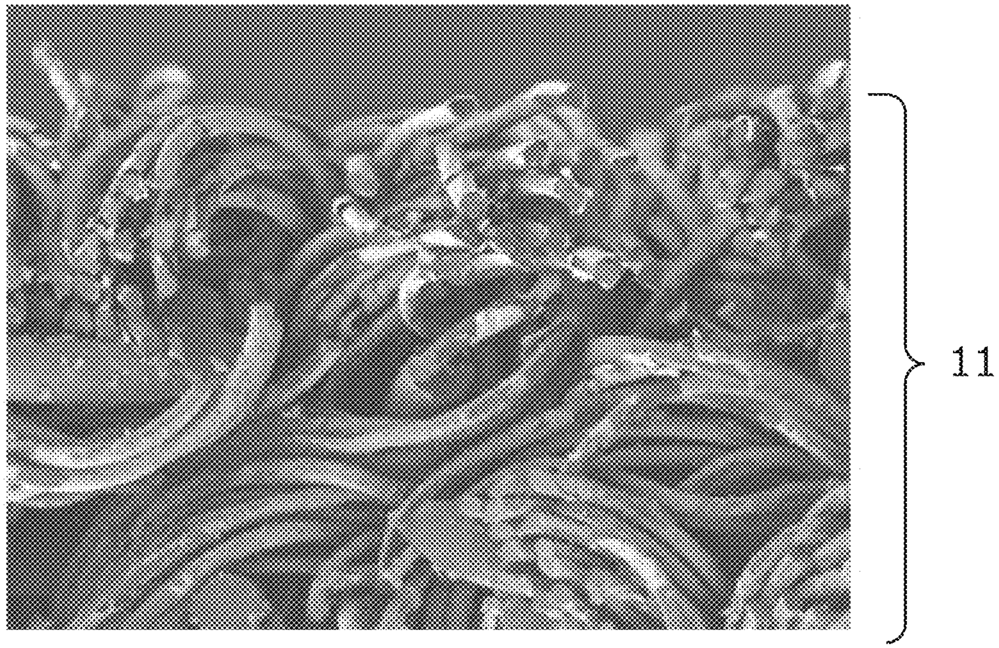
FIG. 20 is an image of a cross-section of the sample A1 that has been treated five times.

FIG. 19 is an image of a surface of the sample A1 that has been treated five times. FIG. 20 is an image of a cross-section of the sample A1 that has been treated five times. The prescribed number of times of imaging is 5. As illustrated in FIGS. 19 and 20, the treatment from step S103 to step S105 described above was repeated five times, and the damage to silver plating was observed in the sample A1.

Figure 21:
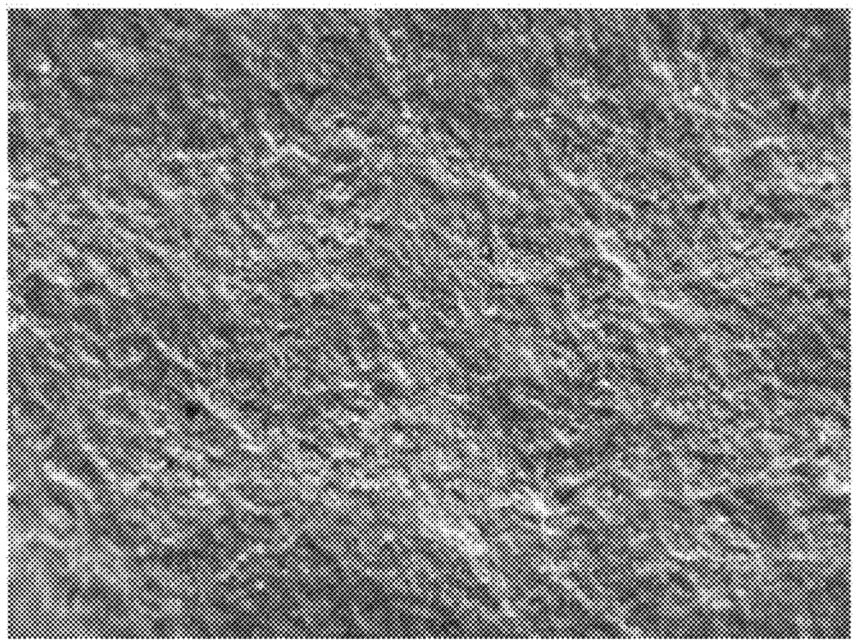
FIG. 21 is an image of a surface of an untreated sample A2.
Figure 22:
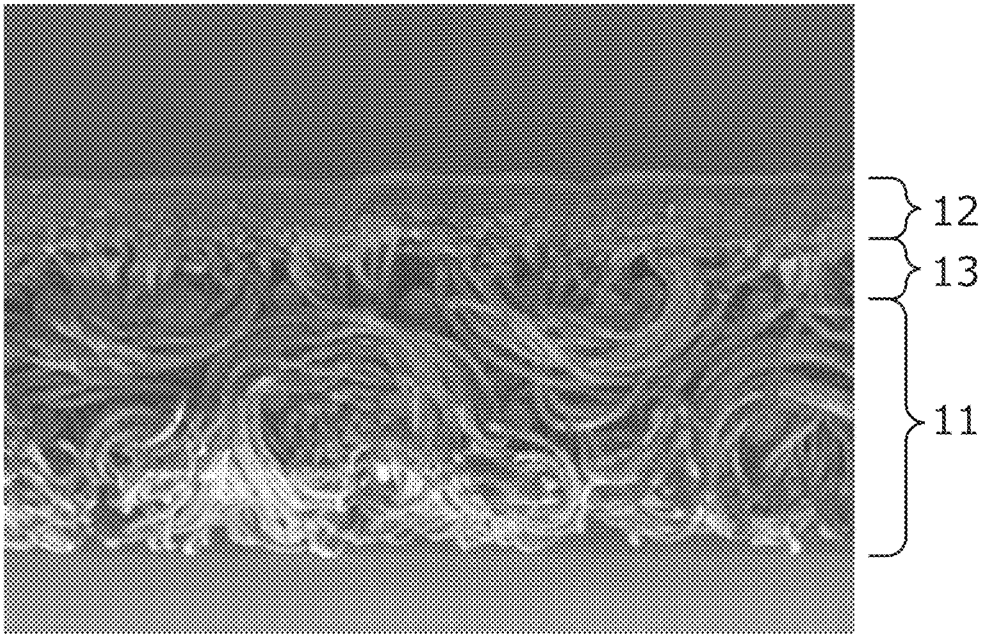
FIG. 22 is an image of a cross-section of the untreated sample A2.

On the other hand, FIG. 21 is an image of a surface of an untreated sample A2. FIG. 22 is an image of a cross-section of the untreated sample A2. Since the samples are untreated, the above-described prescribed number of times is 0. As illustrated in FIGS. 21 and 22, in the untreated state, no damage or the like to the silver plating on a fiber surface of the sample A2 was observed. In addition, since the surface of the sample A2 was covered with DuraQ as an example of the conductive elastomer layer 12, the shape of fibers of AGPoss as an example of the conductive fiber fabric layer 11 was not visually recognized. As illustrated in FIG. 22, it was found that the immersion layer 13 was formed between the conductive elastomer layer 12 and the conductive fiber fabric layer 11 in the cross-section of the sample A2. The immersion layer 13 is a layer in which the fibers of AGPoss are immersed in the DuraQ.

Figure 23:
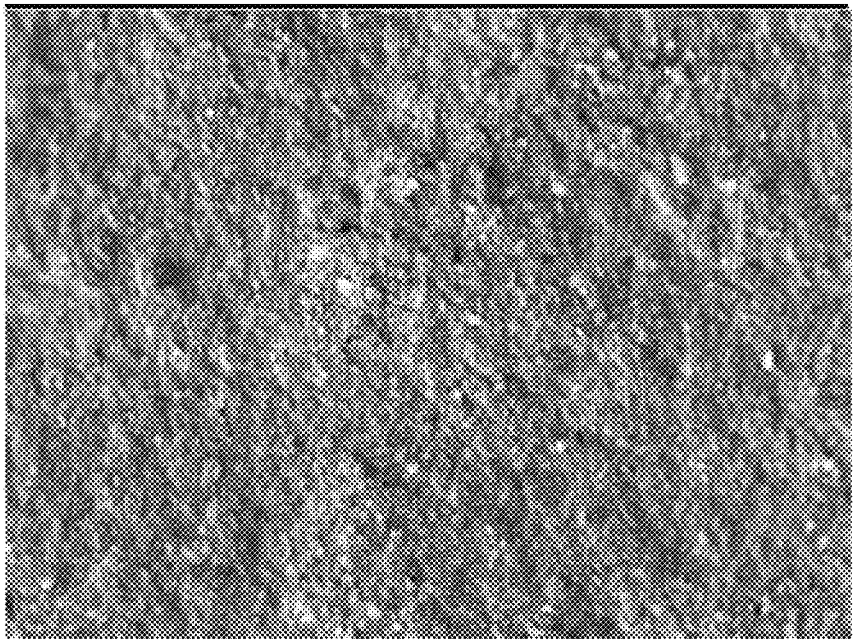
FIG. 23 is an image of a surface of a sample A2 that has been treated five times.
Figure 24:
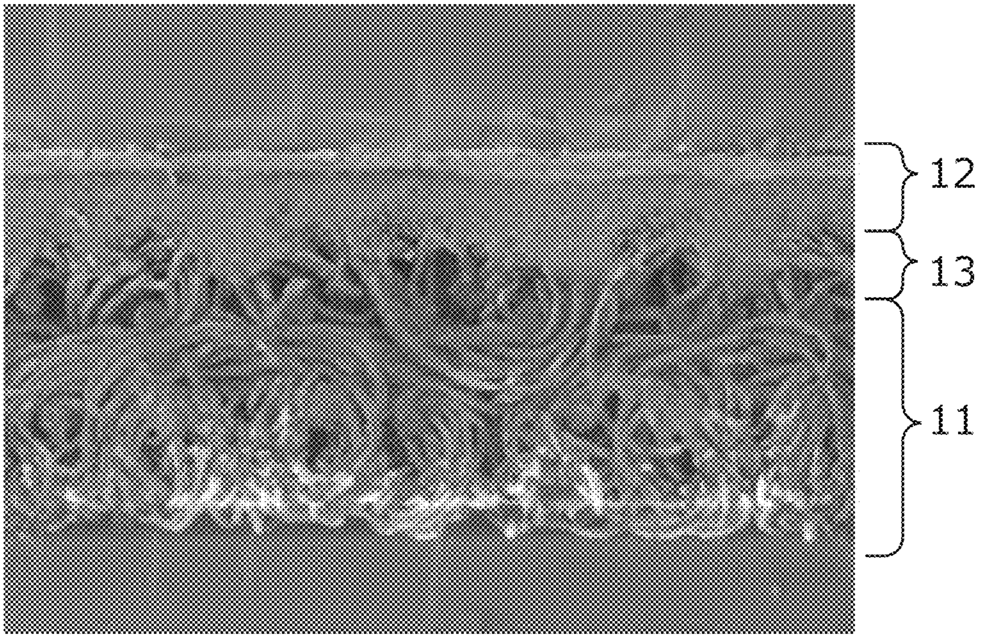
FIG. 24 is an image of a cross-section of a sample A2 that has been treated five times.

FIG. 23 is an image of a surface of a sample A2 that has been treated five times. FIG. 24 is an image of a cross-section of a sample A2 that has been treated five times. The prescribed number of times of imaging is 5. As illustrated in FIGS. 23 and 24, even after repeating the above-described treatment five times, no damage to the silver plating was observed in the sample A2. Even after the five treatments, the above-described immersion layer 13 did not disappear.

<Experiment B (Durability Experiment of Electrode)>

An experiment has shown that the above-described electrode 1 has improved durability against washing due to the presence of the conductive elastomer layer 12. The present inventors have carried out an experiment (hereinafter, referred to as Experiment B) of performing a treatment simulating washing on the sample and evaluating a resistance to the treatment. This resistance was evaluated by measuring sheet resistance of the sample for each treatment time.

The following Table 1 is a table in which a change in sheet resistance of the electrode 1 according to the present invention for each time of washing is recorded. In this table, Sample B2 shows a sheet resistance when the electrode 1 is washed with a commercially available chlorine-based bleaching agent. The electrode 1 in the sample B2 is obtained by printing (applying and drying) the DuraQ onto the surface of the above-described AGPoss.

Further, in this table, the sample B1 indicates sheet resistance when an electrode having the common configuration with the above-described conductive fiber fabric layer 11, is washed with a commercially available chlorine-based bleaching agent. The electrode in the sample B1 was formed of only the above-described AGPoss. In the table, N/D indicates non-detection.

TABLE 1

| Time [min] | Sample B2[Ω/□] | Sample B1[Ω/□] |
|---|---|---|
| 0 | $3.40 \times 10^{-2}$ | $1.34 \times 10^{-1}$ |
| 15 | $8.68 \times 10^{-2}$ | $3.93 \times 10^{-1}$ |
| 60 | $1.08 \times 10^{-1}$ | N/D |
| 180 | $1.06 \times 10^{-1}$ | N/D |
| 300 | $1.56 \times 10^{-1}$ | N/D |

As illustrated in Table 1, in the sample B2, that is, the electrode 1 according to the present invention, the sheet resistance was detected even after being washed with the chlorine-based bleaching agent for 300 minutes. On the other hand, when the sample B1, that is, the electrode not having the conductive elastomer layer 12 was washed with the same chlorine-based bleaching agent, the sheet resistance was not detected in 60 minutes.

Accordingly, it is presumed that the conductive elastomer layer 12 protects the conductive fiber fabric layer 11 and prevents the conductive material from being peeled off due to washing, friction, impact, or the like.

It is presumed that the conductive elastomer layer 12 is broken and loses conductivity when the conductive elastomer layer 12 constitutes the electrode alone. However, in the electrode 1 according to the present invention, the conductive fiber fabric layer 11 is disposed on a lower layer (that is, an outside) of the conductive elastomer layer 12. Therefore, even when the conductive elastomer layer 12 is broken, the conductive fiber fabric layer 11 electrically connected to each of the broken conductive elastomer layers 12 is protected by the conductive elastomer layer 12, so that the conductivity of the electrode 1 is maintained.

In addition, before the washing, the sheet resistance of the conventional electrode (Sample B1) is $1.34\times10^{-1}$Ω/□. On the other hand, before the washing, the sheet resistance of the electrode 1 (Sample B2) according to the present invention is $3.40\times10^{-2}$Ω/□.

That is, while the sheet resistance of the conventional electrode (Sample B1) was about $1\times10^{-1}$Ω/□, the sheet resistance of the electrode 1 according to the present invention (Sample B2) has been improved to about $1\times10^{-3}$Ω/□. That is, the sheet resistance of the electrode 1 is lower than that of the conventional electrode. This is considered to have an effect of the immersion layer 13 in addition to an effect of the conductive elastomer layer 12.

<Experiment C (Linen Washing Experiment Using Actual Machine)>

The present inventors have carried out an experiment (hereinafter, referred to as Experiment C) by actually washing the samples, measuring a surface resistance value of the samples for each number of times of washing, and evaluating the samples.

The washing in Experiment C was performed for 10 minutes at a preliminary washing temperature of 40° C. and a main washing temperature of 80° C. This washing was performed using a commercial washing machine, SWX-60WU, manufactured by Tokyo Sanyo Kikai Co., Ltd. As a detergent, 300 milliliters of 30 w/v % sodium hydroxide was used each time. It was expected that pH was 10 when the detergent was used. In addition, in this washing, 300 milliliters of 35 w/v % hydrogen peroxide was used for each washing. The drying performed for each washing was performed by heating the samples at 80° C. for 13 minutes.

The following Table 2 is a table in which a surface resistance value of the electrode is recorded for each number of times of washing the clothing C according to the present invention. In this table, a sample C2 shows a surface resistance value of the electrode 1 when the clothing C is washed using a linen actual machine. The electrode 1 in the sample C2 was obtained by applying and drying the above-described DuraQ on the surface of the above-described AGPoss, and a thickness thereof was equivalent to 6 masks.

The DuraQ used herein indicates a thickness in a unit of a mask. The mask is a layer having a thickness of 125 μm (micrometer) per one layer. Therefore, since the sample C2 is equivalent to 6 masks, the sample C2 has a layer (conductive elastomer layer 12) of the DuraQ having a thickness of 750 μm (micrometer). In addition, in the sample C2, as the conductive paste, which is a precursor of the DuraQ, a conductive paste having a concentration of the conductive filler of 71% by mass was used.

Further, in this table, the sample C1 indicates a surface resistance value of the electrode when clothing, which is provided with the electrode having the common configuration with the above-described conductive fiber fabric layer 11, is washed using the linen actual machine. The electrode in the sample C1 was formed of only the above-described AGPoss. In the table, O/L indicates that the measurement exceeded an upper limit.

TABLE 2

| Number of times of washing | Sample C1[Ω] | Sample C2[Ω] |
|---|---|---|
| 0 | 7.20e−2 | 2.55e−2 |
| 10 | 8.35e+0 | 4.00e−2 |
| 20 | 7.31e+2 | 3.50e−2 |
| 30 | O/L | 4.50e−2 |
| 40 | O/L | 4.33e−2 |
| 50 | O/L | 4.00e−2 |
| 60 | O/L | 7.17e−2 |
| 70 | O/L | 7.40e+1 |

Figure 25:
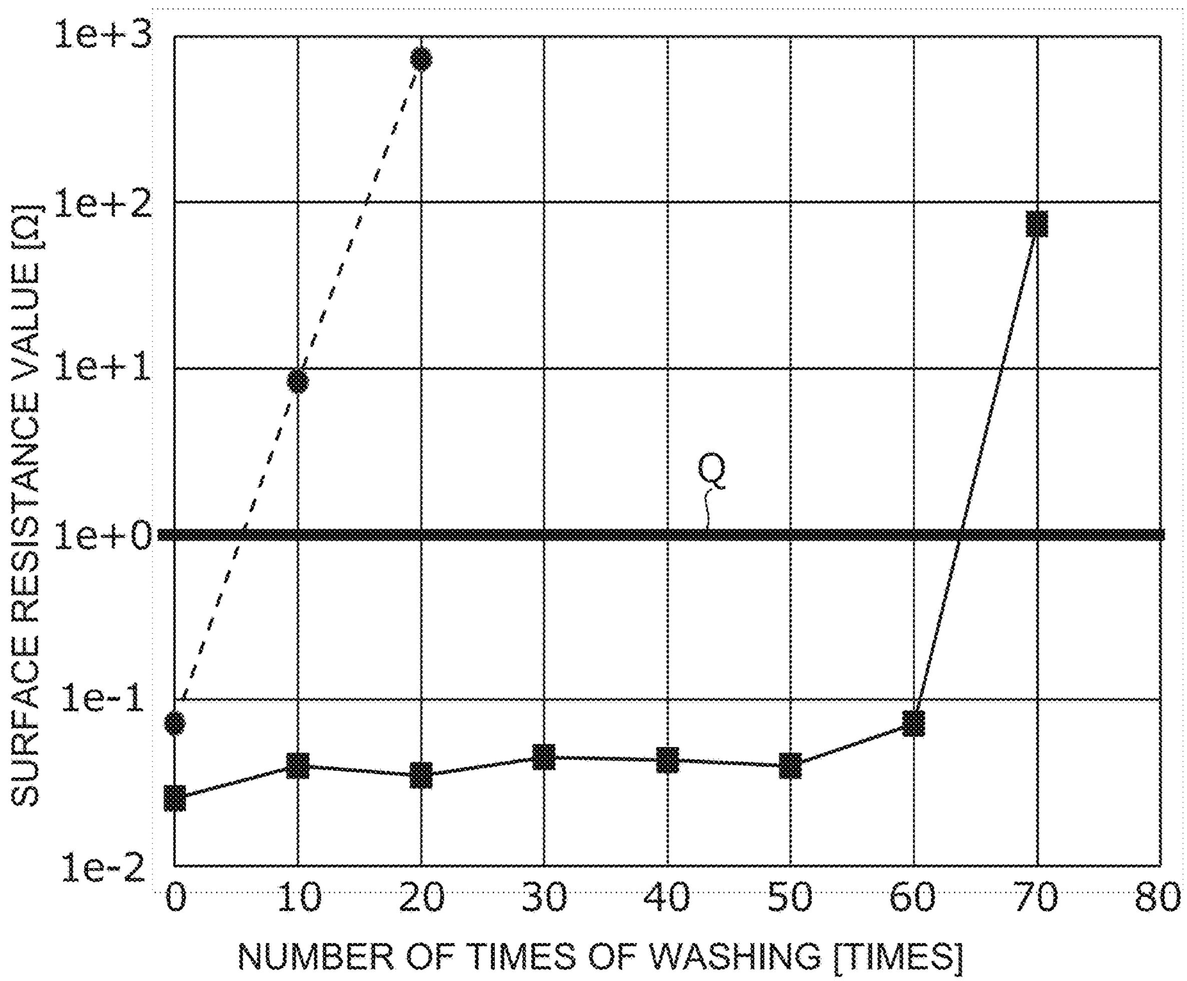
FIG. 25 is a graph illustrating Table 2.

FIG. 25 is a graph illustrating Table 2 described above. In FIG. 25, a reference line Q is a line indicating a surface resistance value of 1.0Ω (ohm), and indicates a quality standard of the electrode. When the surface resistance value is lower than the reference line Q, the electrode satisfies the quality standard. On the other hand, when the surface resistance value of 1.0Ω (ohm) or more indicated by the reference line Q is measured, the electrode does not satisfy the quality standard.

The graph indicated by a broken line in FIG. 25 represents measurement results of the sample C1 in Table 2. As illustrated in FIG. 25, the sample C1 does not satisfy the quality standard at the time point where 10 times of washing has been performed, and the surface resistance value exceeds the upper limit of measurement when the number of times of washing exceeds 30 times. That is, the sample C1, which is formed of only the AGPoss as an example of the conductive fiber fabric layer 11, does not satisfy the quality standard only by performing 10 times of washing.

On the other hand, the graph indicated by a solid line in FIG. 25 represents measurement results of the sample C2 in Table 2. As illustrated in FIG. 25, the sample C2 satisfied the quality standard even at the time point where 60 times of washing has been performed, and did not satisfy the quality standard only after more than 70 times of washing is performed. That is, the sample C2 as an example of the electrode 1 according to the present invention satisfies the quality standard even when the washing is performed 60 times.

<Experiment D (Noise Resistance Experiment)>

The present inventors have carried out an experiment (hereinafter, referred to as Experiment D) of verifying noise resistance by using the electrode 1 according to the invention of the present application. The samples used in Experiment D were a sample D1 as an example in the related art and a sample D2 including the electrode 1 as an example according to the invention of the present application.

The sample D1 was a belt provided with an electrode formed of only the conventional conductive fiber fabric layer 11. The sample D2 was a belt provided with the electrode 1 according to the invention of the present application, in which a paste was applied to the conductive fiber fabric layer 11 and dried to form the conductive elastomer layer 12. In this case, the conductive fiber fabric layer 11 is the above-described AGPoss. In addition, the conductive elastomer layer 12 is the above-described DuraQ.

A subject wears the sample D1 and the sample D2 such that the electrodes are located in the detection region F2 illustrated in FIG. 9, and performs four types of designated operations to measure electrocardiogram in each state. The state of the subject refers to four states of "walking," "standing," "sitting," and "free."

The "walking" in Table 3 refers to a state of walking according to a tempo of 80 beats set by a metronome. The "tempo 80" herein is the number of beats per minute, and is also referred to as 80 beats per minute (bpm). That is, the walking subject walks 80 steps in 1 minute.

Further, the "standing" in Table 3 refers to a state of being stationary in a standing posture. The "sitting" in Table 3 refers to a state of being stationary in a sitting position. The "free" in Table 3 refers to a state in which an action is performed without particularly limiting the operation. Each state was observed for 5 minutes.

The observation was performed by extracting an R-wave from an electrocardiogram waveform in each state of a subject who wears each sample, and determining whether or not the R-wave was a normal value to obtain a proportion of the normal value of the R-wave. The numerical values illustrated in Table 3 are percentages (referred to as a normal rate of the R-wave) with all the acquired R-waves as the denominator and the R-waves determined as the normal values as the numerator.

TABLE 3

| State of subject | Sample D1 | Sample D2 |
|---|---|---|
| Waking | 24.5% | 24.8% |
| Standing | 84.0% | 82.2% |
| Sitting | 96.4% | 95.5% |
| Free | 96.0% | 92.4% |

As illustrated in Table 3 described above, no significant difference was observed in the normal rate of the R-wave between the sample D1 and the sample D2. Therefore, it was found that the electrode 1 according to the present invention exhibited the same degree of noise resistance as compared with the electrode formed of only the conventional conductive fiber fabric layer 11.

<Experiment E (Detection Region Comparison Experiment)>

The present inventors have carried out an experiment (hereinafter, referred to as Experiment E) to compare an influence of detection regions, which make contact with the electrode 1 according to the invention of the present application, on the noise resistance. Experiment E was performed by wearing by a user the electrode included in the sample D2 used in the above-described Experiment D such that the electrode was located in the detection region F1 illustrated in FIG. 9 and the detection region F2 illustrated in FIG. 10.

Table 4 below is a table showing observation results in Experiment E. Experiment E1 in Table 4 is data obtained by disposing the electrode of the above-described sample D2 in the detection region F1 (see FIG. 9) of the subject and observing the subject by the normal rate of the R-wave for each state of the subject. In addition, Experiment E2 in Table 4 is data obtained by disposing the electrode of the sample D2, which is common to Experiment E1, in the detection region F2 (see FIG. 10) of the subject and observing the subject by the normal rate of the R-wave for each state of the subject.

TABLE 4

| State of subject | Experiment E1 | Experiment E2 |
|---|---|---|
| Waking | 98.2% | 24.8% |
| Standing | 99.2% | 82.2% |
| Sitting | 99.5% | 95.5% |
| Free | 99.7% | 92.4% |

As illustrated in Table 4 described above, in all the states of the subject, Experiment E1 exhibited a more excellent noise resistance than Experiment E2. That is, it was clarified that, as compared with a case where the electrode was disposed in the detection region F2 illustrated in FIG. 10, noise was significantly reduced in a case where the electrode was disposed in the detection region F1 illustrated in FIG. 9.

DESCRIPTION OF REFERENCE NUMERALS

1: electrode
11: conductive fiber fabric layer
110: surface
111: conductive composite yarn
1110: elastic fiber
1111: conductive fiber
1111*a*: lower winding yarn
1111*b*: upper winding yarn
12: conductive elastomer layer
120: elastomer composition
121: conductive filler
12*a*: first conductive elastomer layer
12*b*: second conductive elastomer layer
13: immersion layer
2: insulating fiber fabric
21: insulating fiber
2*a*: belt member
E: xiphoid process
F1: detection region
F2: detection region
r5: fifth rib
r6: sixth rib
r7: seventh rib
r8: eighth rib

The invention claimed is:

1. Clothing comprising:
a clothing material worn by a wearer; and
an electrode provided at a position on a surface of the clothing material making contact with a body of the wearer upon wearing, wherein the electrode includes a conductive fiber fabric layer which is a fiber fabric having conductivity and has a first surface contacting said surface of the clothing material and a second surface opposite to the first surface, and a conductive elastomer layer formed on the second surface of the conductive fiber fabric layer and including an elastomer composition and a conductive filler, and when viewed from a direction transverse to a stacking direction of the conductive elastomer layer and the conductive fiber fabric layer, the conductive elastomer layer extends beyond a plane formed by the outermost edge of the second surface of the conductive fiber fabric layer.

2. The clothing according to claim 1, wherein the electrode is provided at a position that makes contact with a site of a torso of the wearer at the same height as a xiphoid process.

3. A belt comprising:

a belt member having stretchability; and an electrode provided at a position on a surface of the belt member making contact with a body of a wearer when the belt member is wound around the wearer, wherein the electrode includes a conductive fiber fabric layer which is a fiber fabric having conductivity and has a first surface contacting said surface of the clothing material and a second surface opposite to the first surface, and a conductive elastomer layer formed on the second surface of the conductive fiber fabric layer and including an elastomer composition and a conductive filler, and when viewed from a direction transverse to a stacking direction of the conductive elastomer layer and the conductive fiber fabric layer, the conductive elastomer layer extends beyond a plane formed by the outermost edge of the second surface of the conductive fiber fabric layer.

4. The belt according to claim 3, wherein the electrode is provided at a position that makes contact with a site on a torso of the wearer at the same height as a xiphoid process.

5. The clothing according to claim 1, wherein the conductive filler is a conductive powder.

6. The clothing according to claim 1, further comprising an immersion layer formed between the conductive fiber fabric layer and the conductive elastomer layer.

7. The clothing according to claim 1, wherein the conductive elastomer layer is formed by applying a conductive substance onto the conductive fiber fabric layer.

8. The belt according to claim 3, wherein the conductive filler is a conductive powder.

9. The belt according to claim 3, further comprising an immersion layer formed between the conductive fiber fabric layer and the conductive elastomer layer.

10. The belt according to claim 3, wherein the conductive elastomer layer is formed by applying a conductive substance onto the conductive fiber fabric layer.

* * * * *